United States Patent [19]
Weihe et al.

[11] Patent Number: 4,655,076
[45] Date of Patent: Apr. 7, 1987

[54] MOISTURE MEASURING APPARATUS

[75] Inventors: Gary R. Weihe, Fremont; Roger D. Lion, Menlo Park, both of Calif.

[73] Assignee: Raychem Corporation, Menlo Park, Calif.

[21] Appl. No.: 573,230

[22] Filed: Jan. 23, 1984

[51] Int. Cl.[4] .......................................... G01N 19/10
[52] U.S. Cl. ............................................ 73/73; 73/337
[58] Field of Search ........................... 73/73, 76, 337; 340/602, 604, 620; 239/63

[56] References Cited

U.S. PATENT DOCUMENTS

| | | | |
|---|---|---|---|
| 2,878,671 | 3/1959 | Prosser et al. | 73/73 |
| 3,117,442 | 1/1964 | Brooks | 73/73 |
| 3,273,849 | 9/1966 | Hansson | 251/4 |
| 3,407,608 | 10/1968 | Whitehead | 405/37 |
| 3,512,712 | 5/1970 | Benesch | 239/63 |
| 3,750,688 | 8/1973 | Hall et al. | 137/2 |
| 3,867,837 | 2/1975 | Malin | 73/73 |
| 3,874,590 | 4/1975 | Gibson | 73/73 |
| 3,906,469 | 9/1975 | Kronk | 340/870.27 |
| 3,916,678 | 11/1975 | Lohoff | 73/73 |
| 4,024,882 | 5/1977 | Haigh et al. | 137/2 |
| 4,051,628 | 10/1977 | Knapp et al. | 47/48.5 |
| 4,098,121 | 7/1978 | Captain | 73/337 |
| 4,107,604 | 8/1978 | Bernier | 324/208 |
| 4,120,813 | 10/1978 | Hatanaka et al. | 252/194 |
| 4,150,571 | 4/1979 | Hayes et al. | 73/336.5 |
| 4,151,833 | 5/1979 | Polishuk | 128/738 |
| 4,182,357 | 1/1980 | Orustein | 239/63 |
| 4,214,701 | 7/1980 | Beckmann | 239/63 |
| 4,286,754 | 9/1981 | Jones | 239/6 |
| 4,489,603 | 12/1984 | Fukami | 73/337 |

FOREIGN PATENT DOCUMENTS

| | | | |
|---|---|---|---|
| 1251838 | 11/1971 | United Kingdom . | |
| 855466 | 8/1981 | U.S.S.R. . | |
| 0883728 | 11/1981 | U.S.S.R. | 73/73 |
| 0966571 | 10/1982 | U.S.S.R. | 73/73 |

Primary Examiner—Charles Frankfort
Assistant Examiner—Thomas B. Will
Attorney, Agent, or Firm—Edith A. Rice; Herbert G. Burkard

[57] ABSTRACT

An apparatus for measuring the moisture content of soil includes a chamber having a water-swellable material in the chamber, the chamber being sized so that the water-swellable material can swell to its fully swollen state, with the external resistance, if any, against the swelling being substantially constant. The device includes a device for transmitting water to the water-swellable material so that it is in equilibrium with the environment. A sensor responsive to the volume of the water-swellable material is provided to indicate the water content of the environment exterior of the apparatus. The preferred sensor is a magnet moveable by the water-swellable material and a Hall effect sensing device.

7 Claims, 9 Drawing Figures

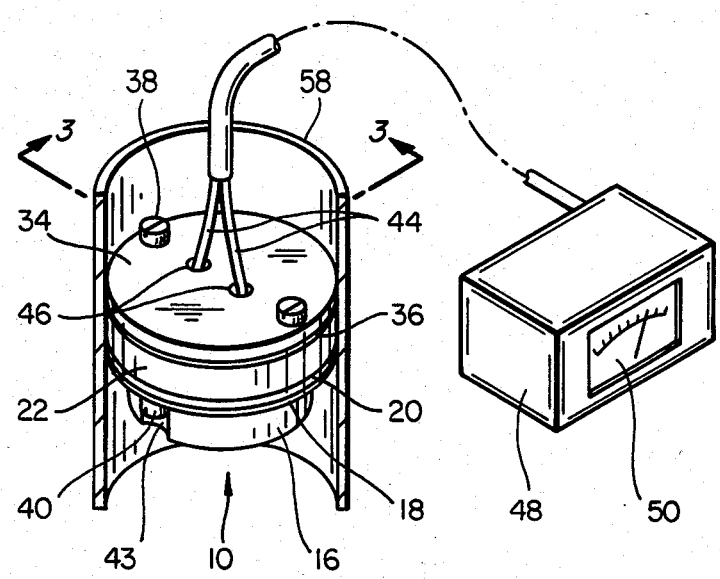
FIG_1
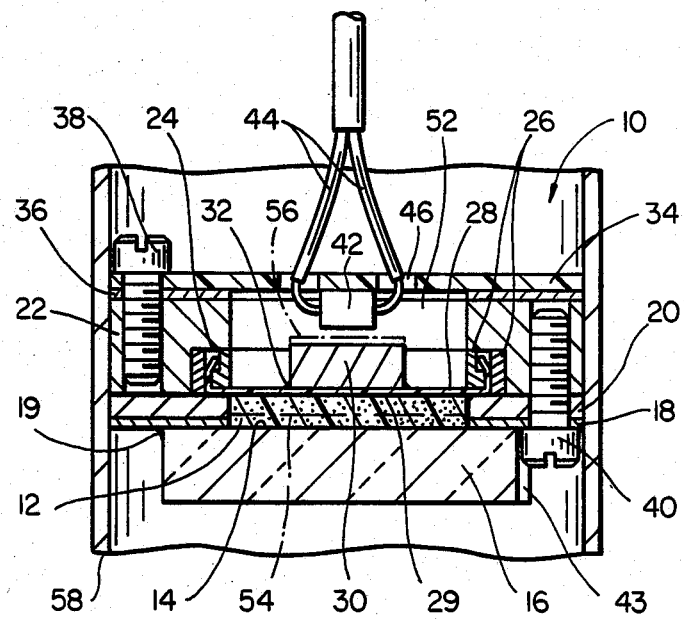
FIG_3

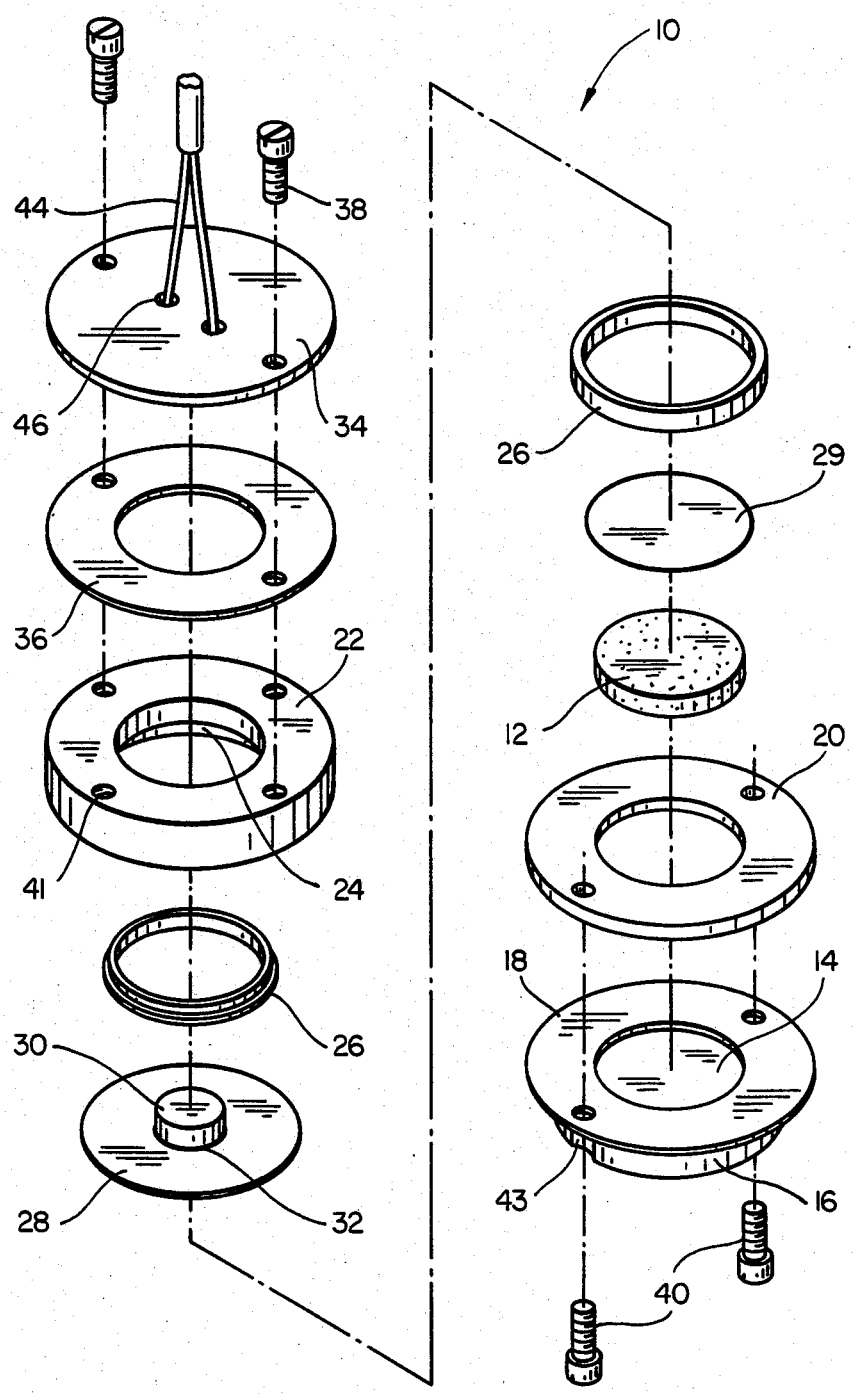
FIG_2

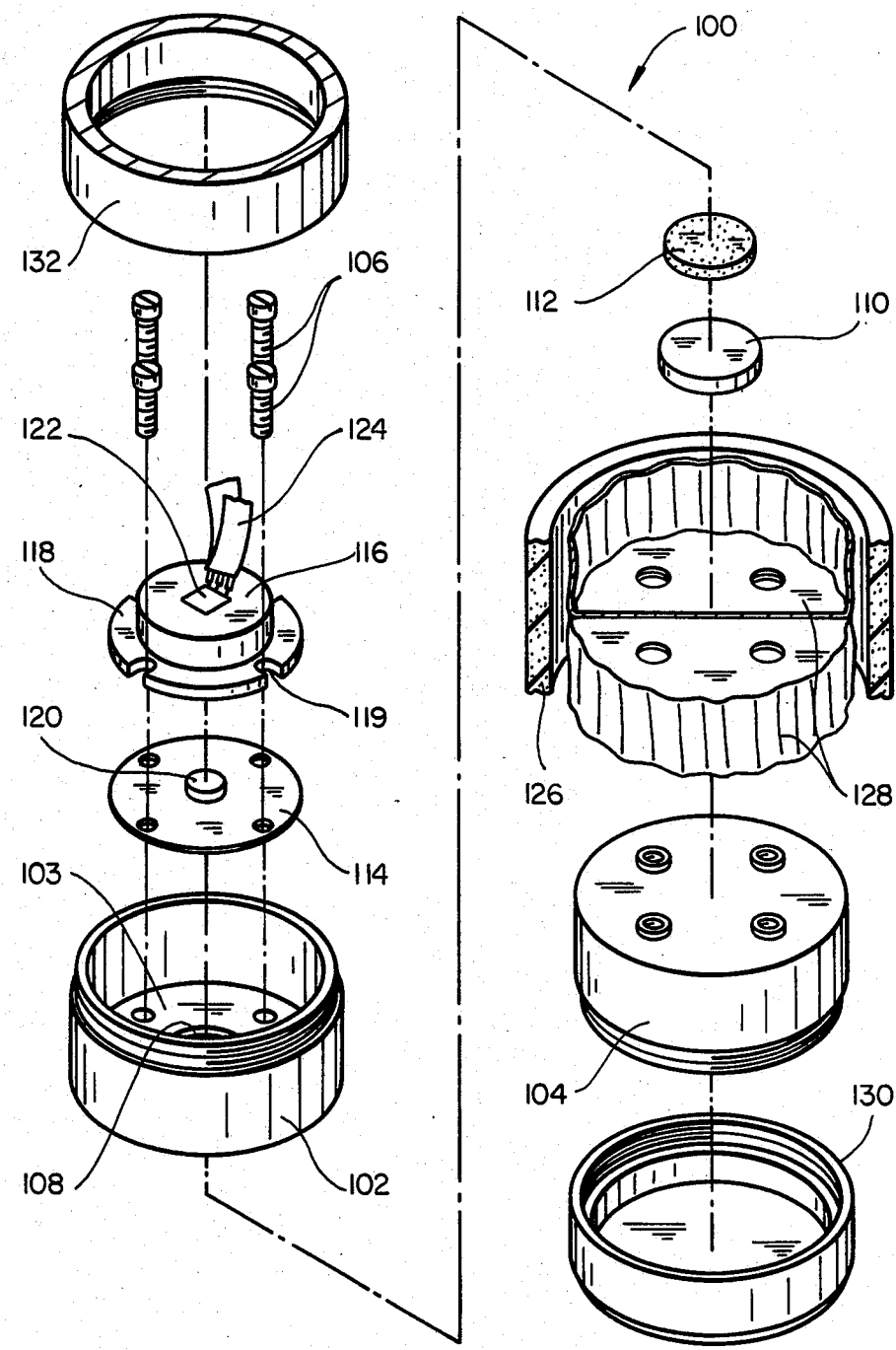
FIG_4

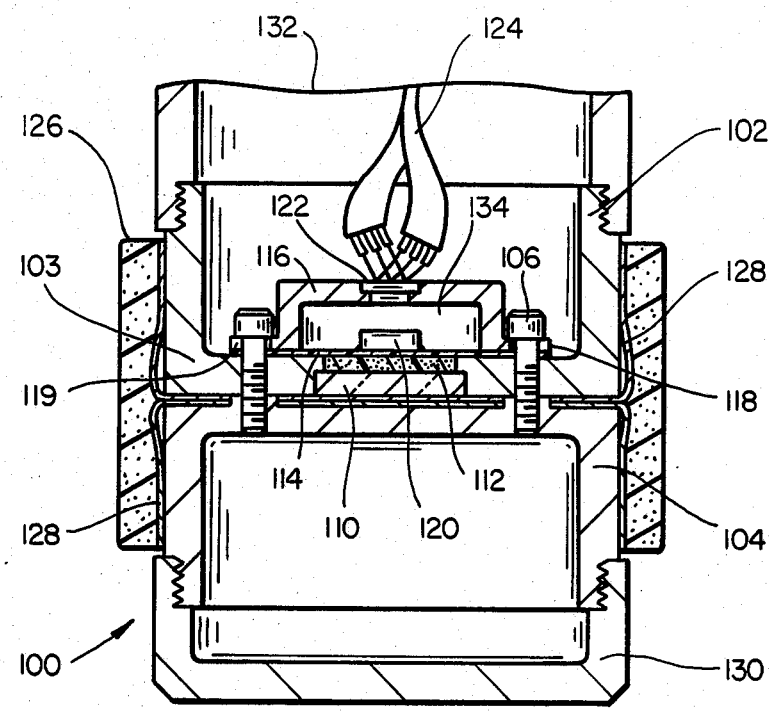
FIG_5
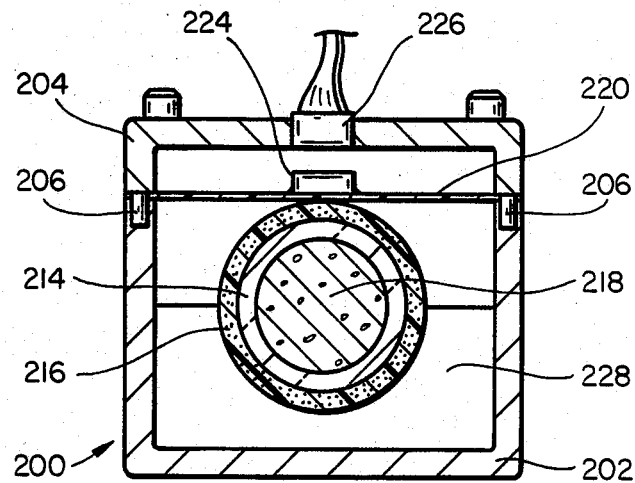
FIG_7

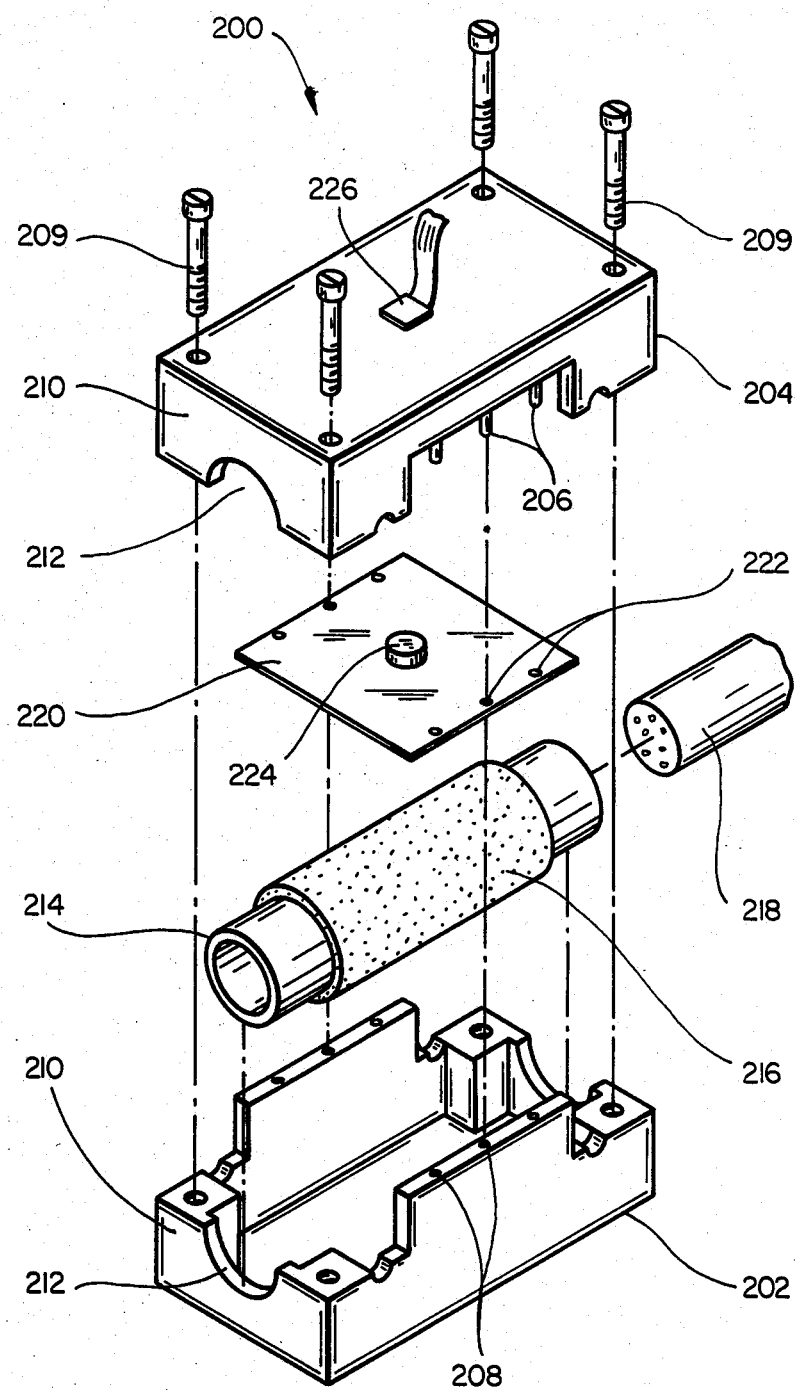
FIG_6

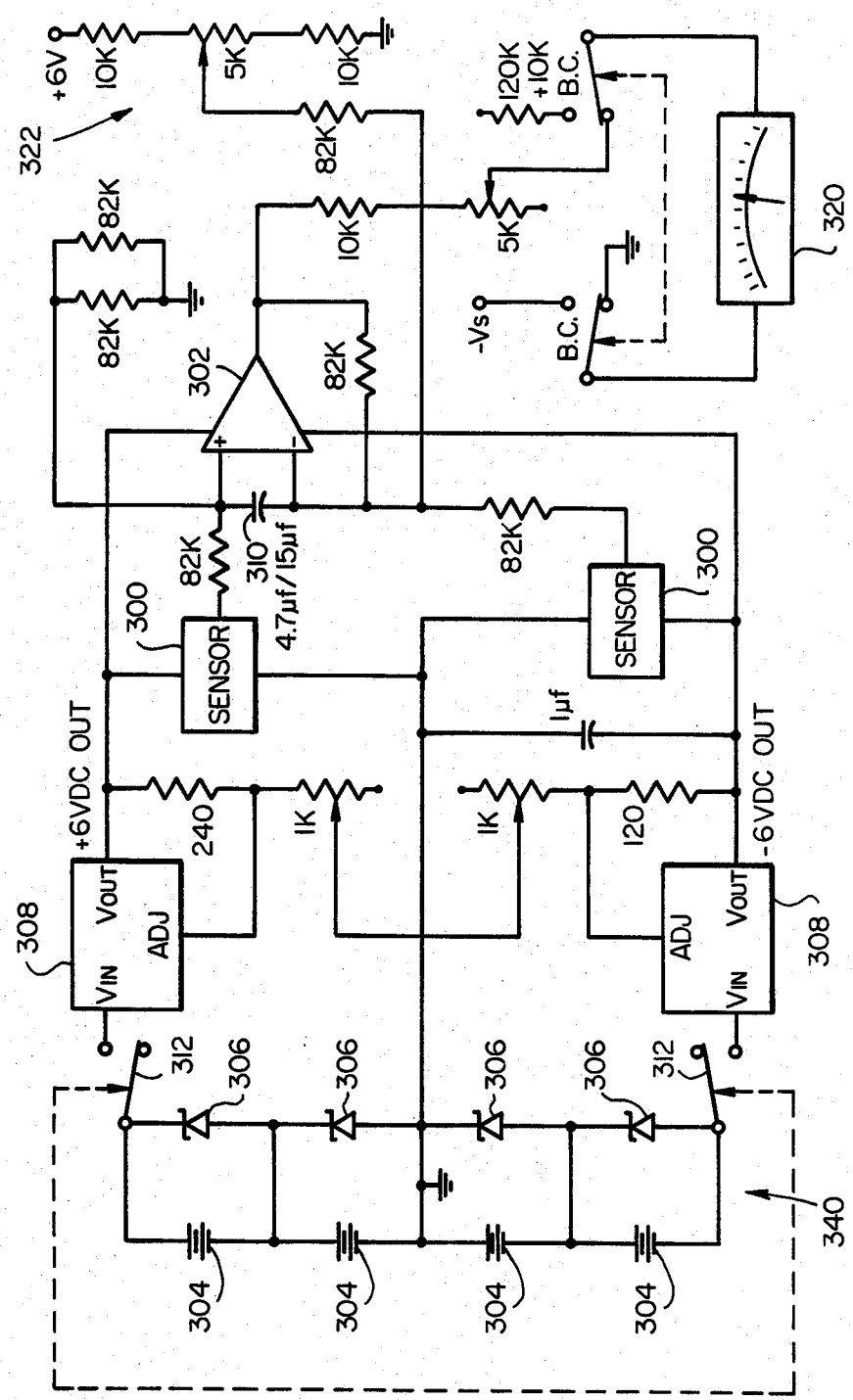
FIG_8

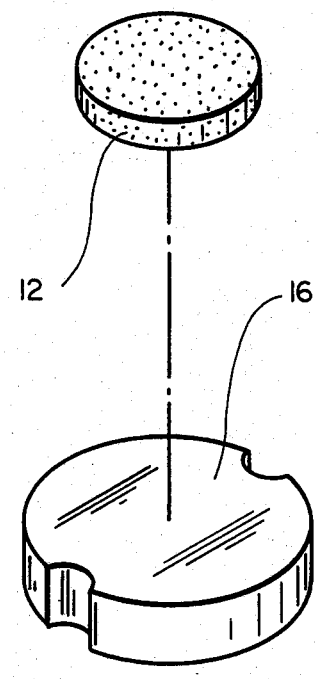
FIG_9

MOISTURE MEASURING APPARATUS

BACKGROUND

The present invention is directed to a humidity measuring apparatus, and in particular an apparatus for measuring the moisture content of soil.

With the expected doubling of the world population in the next 40 years from the current level of 4.7 billion, food production will need to at least double to maintain the nutritional levels already considered inadequate in many countries. In many areas of the world, the availability of water resources and the cost of pumping irrigation water restricts food production. More efficient use of water is needed to meet the demand for increased food production.

One area where water resource efficiency can be improved is irrigation. Irrigation brings at least four potential benefits. It brings under cultivation arid lands, increases yields per acre per crop, allows more than one crop to be grown per year, and reduces risk of crop failure.

The soil parameter which controls whether or not the soil requires irrigation is the soil matric potential. A soil matric potential of 0 corresponds to soil completely saturated with water. Two important soil matric potential values with respect to plant growth are the field capacity at about −0.3 bar and the permanent wilting point at about −15 bars. At soil matric potentials from −0.3 bars to 0 bar the air channels in the soil are progressively filled with water. Since the roots need both oxygen and water for growth at soil matric potentials above −0.3 bar and close to zero the plant is under stress and in the worst case, i.e. soil matric potential of zero, the plant dies. As the soil matric potential drops below −0.3 bar, i.e. −0.3 bar to −15 bars, the plants must use more of their energy to extract water from the soil which places them under stress and limits growth and yield. At about −15 bars the roots can no longer extract water from the soil and the plant wilts and dies. The optimum soil matric potential for most crops and soil types is, therefore, from field capacity at about −0.3 bar to about −3 bars, below which most plants are under extreme stress. In many cases −0.3 bar to −1 bar is preferred.

A reliable soil moisture sensor should have high preferably from 0 to −15 bars. Optimum growth occurs close to field capacity (about −0.3 bar) but the grower should be able to let the field dry approaching the permanent wilting point without worrying about crop loss when either he is experiencing a water shortage, is close to harvest, or is trying to optimize his yield to water cost relationship.

It is been found difficult to develop a reliable soil moisture sensor in the range of −0.3 to −1 bar because these values correspond to a relative humidity in salt free soil of 99.98% and 99.93%, respectively. Any device designed to sense soil moisture levels should have a large response between 99.9 and 100% relative humidity.

A variety of techniques are currently used to determine soil moisture content, all of which have significant disadvantages. In one technique, an auger soil probe is drilled into the ground to withdraw a soil sample. The amount of moisture is estimated by feeling the withdrawn sample by hand, but for accurate measurement, the sample is sealed in plastic and sent to a laboratory. This probe method is time-consuming and laborious, particularly if it needs to be done daily over a large area.

Another technique to measure soil matric potential uses a tensiometer. In this technique, a porous cup filled with water is buried at the main level of the root zone. Water moves in or out of the cup in response to soil moisture level. A tube connects the cup to a vacuum gauge or a mercury manometer. The readings indicate the soil matric potential. Tensiometers are labor intensive, require readings in the field daily, and must be maintained with periodic additions of water. Further, they only cover the range of soil matric potential of 0 to about −0.8 bar.

Another technique utilizes electrical resistance blocks made of gypsum plaster of paris with two electrodes embedded in the block. The porous block is buried in the soil, and the wires from the electrodes are connected to a meter that gives a reading of the electrical resistance between the electrodes. The main problem with these blocks is that soil salinity affects the reading, and thus these blocks require extensive calibration and can degrade in some soil environments.

Another technique used is a neutron probe using a radioactive isotope, usually americium, to measure water content. Tubes are installed in the soil at the desired depth. The probe is inserted into the tube and the amount of back scatter from protons in the soil is measured. A problem with neutron probes is they must be calibrated for each soil type since they measure total water, some of which is not available water for plant growth, as it is chemically bound or otherwise not available to the plant. They also must be calibrated for soil depth because soil composition varies with depth. In addition, a neutron probe is expensive, costing in excess of $3,000, is radioactive, and must be used by a skilled technician.

Infrared sensors can be used to differentiate stressed plants from healthy plants because the temperature of the green leaves of stressed plants is higher than the temperature of leaves of healthy plants. A problem with infrared sensors is that they do not differentiate between water, salt, insect, and disease stresses. In addition, they are expensive, costing about $2,500.

Another measuring system used is a heat dissipation sensor, usually made of a ceramic body containing a heater and a thermocouple. The heat capacity of a ceramic body is a function of its water content which is proportional to the water content of the adjacent soil. In this technique, the heater in the ceramic body is activated for about one minute, and the temperature increase of the sensor is measured. The measured temperature increase is proportional to the heat capacity of the ceramic body, and therefore, the water content of the soil. Heat dissipation sensors have poor sensitivity, and are costly, requiring extensive calibration.

A variety of devices have been developed for automatically controlling irrigation which depend on the moisture content of the soil to be irrigated. For example, Ornstein in U.S. Pat. No. 4,182,357 describes a valve containing a water-swellable polymer that swells against a compressible water line, closing off the water line as the polymer swells. The Ornstein device is designed to control at a specific soil matric potential. For example, if it is designed for −0.3 bar or field capacity then water flows to the soil at soil matric potentials below −0.3 bar. At soil matric potentials above −0.3 bar water does not flow. The Ornstein device is essentially an on/off device designed for a specific soil matric potential value. A device that provides an indication of the moisture content of soil over a much wider range would be more valuable.

Several problems exist with this device. The first is that it requires a constant water supply, i.e. water pressure. If it does not have a constant water pressure it can dry out at soil matric potentials below −0.3 bar and when the water is turned on a flooding condition can occur. Another problem with the Ornstein device is that once the device is built for a given soil moisture potential, the device can not be varied. This takes the control out of the hands of the grower. The grower needs a system which will allow him to control field irrigation based upon his strategy on how to use his allotted irrigation water when it is available to him. He needs to sequence the irrigation of his field, determine how much to apply, and when to apply it. The data he needs include knowledge of soil moisture conditions over the range of soil matric potential from 0 to −15 bars.

SUMMARY

The present invention is directed to an apparatus capable of measuring the moisture content of soil that overcomes disadvantages of the prior art techniques. An apparatus capable of measuring the moisture content of soil according to the present invention comprises a chamber with a water-swellable material substantially completely contained in the chamber. The water-swellable material has a fully swollen volume in its fully swollen state when in equilibrium with water of at least about 2 times its dry volume. The chamber is sufficiently large to accommodate the water-swellable material in its fully swollen state. The external resistance, if any, to swelling remains substantially constant as the water-swellable material swells to its fully swollen state.

The apparatus includes means, such as a porous ceramic member, for transmitting (i) water to the water-swellable material from the environment exterior to the apparatus and (ii) water from the water-swellable material to the environment exterior to the apparatus.

Sensing of the volume changes can be effected by a variety of techniques. A combination of a detector and an activator for the detector can be used. The detector can be fixed with the activator moving with respect to the detector in response to swelling and shrinkage of the water-swellable material. Alternatively the activator can be fixed with the detector doing the moving. The sensor can be a Hall effect sensor that is responsive to a magnet activator that moves in response to swelling and shrinkage of the water-swellable material. The magnet can be mounted on a compliant containing means such as a membrane that moves in response to swelling and shrinkage of the water-swellable material.

Preferably the water-swellable material is a polymer anchored to a rigid reference member so that the distance between the sensor and the magnet can be correlated with the amount of swell of the polymer. The rigid reference member can be a rigid ceramic member used for transmitting water to and from the water-swellable material. In this preferred embodiment, the water-swellable polymer is adhered to the porous member.

In this preferred version, as the water-swellable polymer swells and shrinks, it has a tendency to tear away from the reference member. To minimize this problem, the water-swellable polymer can be a plurality of pieces that can be formed by dicing a section or disk of water-swellable polymer into small pieces.

Preferably the swellable material increases size in the range of from −3 to 0 bars, more preferably from −15 to 0 bars so that the apparatus can indicate the water content of soil over these ranges. For detection of moisture for other than crop irrigation, the apparatus can be employed to detect water content of up to about 100 bars.

In one version of the invention, to insure anchoring between the reference member and the polymer, the reference member can be a rigid, porous cylindrical substrate having a tube of a water-swellable polymer in contact with the substrate. The polymer can be shrunk onto the substrate. A compliant membrane with a magnet secured thereto is placed over the water-swellable polymer and a sensing element such a Hall effect sensor is placed in the housing. As the water-swellable polymer swells and shrinks, the effect of the magnet on the sensor varies with the distance between the magnet and the sensor.

A significant advantage of an apparatus according to the present invention is that it provides accurate readings of the soil moisture content over the total range of soil matric potential values of interest for plant growth, i.e. 0 to −15 bars. The main reason for this is that the water-swellable material is allowed to swell and shrink substantially unrestrained which gives good sensitivity over the entire range of soil matric potential values. Thus, a dimensional change as high as a 30-fold increase over a soil matric potential range of 0 to −15 bars is available. This apparatus allows the grower to control soil moisture matric potential for either optimum growth, keeping his crops alive in times of water shortage, or trying to optimize his yield to water cost relationship.

DRAWINGS

These and other features, aspects, and advantages of the present invention will become better understood with reference to the following description, appended claims, and accompanying drawings where:

FIG. 1 is a front elevation view of an apparatus according to the present invention capable of measuring the moisture content of soil and including a meter responsive to the electrical output from the apparatus;

FIG. 2 is an exploded perspective view of the apparatus of FIG. 1;

FIG. 3 is a sectional view of the apparatus of FIG. 1 taken on line 3—3 of FIG. 1;

FIG. 4 is an exploded perspective view of another apparatus according to the present invention;

FIG. 5 is a sectional view of the apparatus of FIG. 4;

FIG. 6 is an exploded perspective view of another apparatus according to the present invention;

FIG. 7 is a sectional view of the apparatus of FIG. 6; and

FIG. 8 is an electrical schematic of a system providing a readout of the moisture content of soil using the principles of the present invention.

FIG. 9 is an exploded view of a water-swellable material has been diced into a plurality of pieces and attached to a porous member 16.

DESCRIPTION

With reference to FIGS. 1–3, a soil moisture measuring device 10 comprises a disk of a water-swellable polymer 12 adhered to the top surface 14 of a disk of water porous material 16 such as a rigid ceramic disk. The porous member 16 is adhered to the underside of an annular mounting plate 18 with a two part epoxy adhesive 19 such as Devcon 5 Minute Epoxy ™. A lower annular spacing washer 20 sits on the annular mounting plate 18 so that the combined thickness of the lower annular spacing washer 20 and the annular mounting plate 18 are less than the thickness of the disk of water-swellable material 12 in its fully swollen state. The water-swellable material 12 is located within the center of the annular mounting plate and the lower annular spacing washer.

An annular housing member 22 sits on the lower spacer 20. The housing member 22 includes a circular recess 24 at its base in which is located a two part snap ring 26 that holds a compliant membrane 28 above the water-swellable material 12. The water-swellable material 12 is prevented from adhering to the membrane 28 by an anti-adhere sheet 29 which can be made of Teflon ™ coated glass fabric. A magnet 30 is adhered to the top surface of the membrane 28 by an adhesive 32 such as the Devcon adhesive. The moisture measuring device 10 includes a phenolic cover 34 mounted to the top of the housing member 22 with an upper annular spacing washer 36 therebetween. The measuring device 10 is assembled with a pair of upper screws 38 holding the cover 34 and upper spacing washer 36 to the housing 22, and a pair of lower screws 40 holding the mounting plate 18 and the lower spacing washer 20 to the housing 22. The screws 38 and 40 fit through aligned holes in the respective pieces, the holes 41 in the housing 22 being threaded. The porous member 16 includes a pair of grooves 43 in its outer surface for the lower screws 40.

A Hall effect sensor 42 is secured to the underside of the cover 34 directly above the magnet 30. The electrical leads 44 for the Hall effect sensor 42 extend through openings 46 in the cover and lead to a detector 48 with a scale 50 that provides a readout of the moisture content of the environment surrounding the measuring device 10 based on the output from the Hall effect sensor 42. The Hall effect sensor 42 can comprise two Hall effect devices.

The measuring device 10 includes a chamber 52, the boundaries of which are defined by the porous member 16, mounting plate 18, lower spacing washer 20, housing member 22, upper spacing washer 36, and the cover 34. The chamber 52 is the space into which the water-swellable material can swell. Located in the chamber 52 are the water-swellable material 12, membrane 28, anti-adhere sheet 29, and magnet 30. The volume of the water-swellable material 12 when in its fully swollen state is less than the volume of this chamber 52. In FIG. 3, the water-swellable material is shown in its almost fully swollen state. The unswelled polymer is represented by line 54 in FIG. 3. When the water-swellable material 12 is fully swollen, the magnet 30 is in a position near the Hall effect sensor 42 as represented by line 56.

The water-swellable material 16 can swell to its fully swollen state in the chamber 52. By the term "fully swollen state" there is meant the state of the water-swellable material when it is in equilibrium with deionized water, i.e. when the water-swellable material is placed in a beaker of deionized water. The volume of the material in its fully swollen state is referred to as the "fully swollen volume".

The external resistance against such swelling is minimal and substantially constant. The only resistance is that provided by the compliant membrane 28 and the weight of the magnet 30. As the compliant membrane 28 flexes, there is some increase in resistance, but it is minimal. Thus, the water-swellable material 12 can swell to its full extent. The external resistance against swelling is preferably less than about 3 psi, and more preferably less than about 1 psi.

By the term "external resistance" there is meant resistance provided by elements external to the water-swellable material 12 itself. Inherently there is internal resistance against swelling of the water-swellable material, i.e. the water-swellable material itself tends to resist swelling.

Swelling of the water-swellable material 12 occurs principally in one direction. Because of the porous member 16 which is preferably rigid, and fixed in relation to the Hall effect sensors 42, a change in thickness of the material takes place only towards the Hall effect sensors 42. The water-swellable material is applied or adhered to porous member 14 while swollen at least partially. The adhesion between the water-swellable material and the porous member restricts the lateral swelling and shrinkage. Thus, most of the swelling and shrinkage of the water-swellable material occurs in the direction of the Hall effect sensors 42.

In one application where it is desirable to determine moisture content of the soil at different depths it can be advantageous to install more than one measuring device 10 in a common case to facilitate installation and removal. FIG. 1 shows a device 10 contained in a portion of a case 58. To facilitate water transport between the soil and device 10 a water transporting means is required. This can entail a porous transmitting member (not shown) in contact with the porous member 16 and the soil. Contact with the soil could be made through one or more openings in case 58. The case 58 can be provided with a measuring scale and a sharp end so that the measuring device 10 can easily be placed below ground to a selected depth.

The device 10 need not include the compliant membrane 28. However, it is desirable to provide the membrane 28 so that the magnet 30 can be fixedly secured to the membrane so that the lateral position of the magnet 30 relative to the Hall sensor 42 remains unchanged. If the magnet 30 moves laterally, this could affect the output from the sensor 42.

Preferably all of the structural elements of the device 10, including the mounting plate 18, lower spacing washer 20, housing member 22, snap ring 26, cover 34, upper spacing washer 36, and screws 38 and 40 are made from a tough, corrosion resistant material that does not have any effect on the sensitivity and accuracy of the measuring device. Suitable materials include nonmagnetic stainless steel, brass, and rigid polymers, such as acetal resins available under the trademark Delrin from du Pont.

The components are not necessarily to scale in the drawings, and depending upon the particular dimensions of the main components, namely the porous member and the water-swellable material, spacers may or may not be needed. Further, although the measuring device 10 is shown in its preferred orientation with the porous member 16 at the bottom and the water-swellable material 12 swelling upwardly, the device can be oriented in any direction.

The water-swellable material 12 preferably has a swell ratio, which is the ratio of the fully swollen volume of the material to its dry volume, of from about 2 to about 100, preferably about 4 to about 30. The dry volume of the water-swellable material 12 is its volume when the free water, i.e. uncombined water, content of the material 12 is 1% or less by weight. At swell ratios less than about 2, there is inadequate increase in volume to have a satisfactorily sensitive device over the range of soil matric potential of interest. At swell ratios greater than about 100, most of the swelling occurs over a very narrow range of from about 0 to −0.5 bars, which is inadequate for a soil moisture measuring device. Most preferably the swellable material has a swell ratio of from about 10 to less than about 25.

A variety of water-swellable materials 12 can be used, including vegetable fibers such as flax, cotton, and hemp, and polymeric materials. Preferably the water-swellable material can repeatedly swell and shrink by undergoing hydration and dehydration reversibly without hysteresis. In other words, the volume attained by the material when it is in equilibrium with the soil at a given water availability level is substantially the same independent of whether the soil is drying or wetting. The water-swellable material is substantially completely contained in the chamber.

Suitable material-swellable polymers include a wide variety of gels such as polyurethane gels, solid gels derived from polyacrylamide, polyvinyl pyrrolidone, polyethylene oxide, or polyvinyl alcohol, as well as hygroscopic resins comprising a vinyl polymer having an epoxy group as described in U.S. Pat. No. 4,120,813, which is incorporated herein by this reference. Illustrative polymers which can be used as the water-swellable polymer include the following: poly(ethylene oxide); polyvinyl pyrrolidone; polyacrylamide; anionic polyacrylamide; polyvinylalcohol; maleic anyhydride-vinylether copolymers; polyacrylic acid; ethylene-maleic anhydride copolymers; polyvinylethers; dextran; gelatin; hydroxy propyl cellulose; methyl cellulose; carboxymethyl cellulose; hydroxyethylcarboxymethyl cellulose; hydroxyethyl cellulose; propyleneglycol alginate; sodium alginate; polyethyleneimine; polyvinyl alkyl pyridinium halides, e.g. polyvinyl-n-butyl-pyridinium bromide; polyproline; natural starches; casein; proteins; polymethacrylic acid; polyvinylsulfonic acid; polystyrene sulfonic acid; polyvinylamine; ammonium polyacrylates; hydroxyalkyl acrylates; hydroxyalkyl methacrylates; hydroxyalkoxyalkyl acrylates; hydroxyalkoxyalkyl methacrylates; polyethylene oxide adduct esters of acrylic and methacrylic acids; alkoxy acrylates and methacrylates; alkoxyalkyl acrylates and methacrylates; partially hydrolyzed polyacrylamides; poly-4-vinylpyridine; polymerized monoesters of olefinic acids; polymerized diesters of olefinic acids; and acrylamide and difunctional polymerizable materials, e.g. diacids, diesters or diamides; and the like.

These polymers can be cross-linked as required to have the desired degree of stability in water and the required amount of swelling.

These materials can be prepared in a crosslinked state by a variety of techniques. Monomers can be polymerized with crosslinking agents, or the polymers can be crosslinked with condensation agents, such as di- or multivalent metal salts, or chemically, thermally, or by radiation-induced free radical reactions. Some uncrosslinked polymers can also be used. The presence of water-insoluble crystallites, or strong intermolecular interactions can yield an acceptable water-swellable material.

The water-swellable material 12 need not be a single one of these materials but can be mixtures of two or more materials. Also, it is possible to employ copolymers of these materials. For example, copolymers of ethylene oxide and minor or major amounts of other alkylene oxides can be used.

If desired, a wide variety of animal, vegetable, mineral, or synthetic fillers can be employed as fillers in the water-swellable material. These can remain intact in the material or can be dissolved or removed to yield a porous material with decreased swell and shrink times. Fillers such as glass fibers and wood flour are expected to remain and to alter properties such as fully swollen volume, swell time, strength, and swelling anisotropy.

Added fillers can modify the behavior of the water-swellable polymer. For instance, adding a powdered molecular sieve as a filler increases the rate at which the polymer swells. Adding cellulose fibers with the fibers oriented parallel to each other allows expansion in two dimensions but restricts expansion in the direction of the fibers. A water-swellable polymer containing iron powder, coated to prevent rusting, can be used to modify a magnetic field between a Hall effect sensor and a magnet.

The water-swellable material can be provided in a variety of shapes, including the disc shape shown in FIGS. 1–5, the tubular shape shown in FIGS. 6 and 7, which will be described below, powders, rings, spheres, rods and the like. When a disc is used, preferably the disc is from about 0.01 to about 10 mm thick when dry. If the disc is smaller than about 0.01 mm when dry, there can be an inadequate change in thickness upon swelling to provide a useable change in output from the sensor. If the disc is larger than about 10 mm in thickness when dry, the time for the water-swellable material to reach equilibrium with the surrounding environment can be too long. More preferably the disc is from about 0.05 to about 4 mm, and most preferably from about 0.1 to about 2 mm, in thickness when dry.

As discussed above, preferably the water-swellable material is anchored to a reference member so that repeatable readings can be taken. Preferably the reference member is the porous member which can be made rigid for this purpose. One way to mount the water-swellable material on the porous member is to use a polymer that bonds to the porous member. For this, bonding can be effected by casting the polymer in place, and then curing it. Alternatively, a polymer can be placed on the porous member as a syrup and allowed to partially dry before cross-linking. This technique reduces stresses and anisotropy. The cross-linking can be effected with radiation with the polymer dry when radiated.

As shown in FIG. 3, optimally the water-swellable material has a high surface area to volume ratio as provided by a plurality of pieces or fragments, particularly if polyethylene oxide is used as the water-swellable material. Significant advantages result from having a high volume to surface area ratio. For example, a high volume to surface area ratio reduces stress on shrinking. If the water-swellable material were a single piece, the stresses incurred upon shrinkage could be so great that the material could become partly or wholly separated from the porous member 16. Further, small pieces of water-swellable material reach equilibrium with the environment faster than large pieces which results in an apparatus very responsive to changes in soil water content. In addition, with a large piece, air can be trapped between the water-swellable material and the porous member. This is less likely to occur with water-swellable material having a high surface area to volume ratio.

To obtain these advantages, preferably the surface area to volume ratio of the pieces of water-swellable material is at least about 1 mm$^{-1}$ when in their fully swollen state. Generally, the pieces have a surface area to volume ratio of from about 1 to 4000 mm$^{-1}$ when in their fully swollen state, more preferably from about 2 to about 10 mm$^{-1}$, and most preferably from about 2 to about 5 mm$^{-1}$. Fragmentation can be effected by dicing a disc of water-swellable material into checkerboard squares about 3 mm on a side. The dicing takes place when the water-swellable material is substantially fully swollen. FIG. 9 shows this embodiment in which water-swellable material 12 which has been diced into a plurality of pieces is attached to the porous member 16. The plurality of pieces minimizes the tendency of the water-swellable material to tear away from the porous member 16.

The porous member 16 serves to transmit water reversibly between the water-swellable material 12 and the environment. It protects the water-swellable material from direct contact with soil, and preferably provides a rigid support for the water-swellable material. Rigid porous members include sintered polymers such as polyethylene, polypropylene, and Teflon ™, where the Teflon is modified to enhance wettability such as by chemical etching; concrete; ceramics such as aluminum oxide; glass frit; and sintered metals. A preferred porous ceramic member is made of aluminum oxide and is rated at 1 bar and can be obtained from Soil Moisture Equipment Company of Santa Barbara, Calf., Catalog No. 604D01-B1M1.

The means used for transmitting water reversibly to and from the water-swellable material is non-swellable. By "non-swellable" there is meant that the fully swollen volume of the transmitter is less than 2 times the dry volume of the transmitter.

The compliant membrane 28 serves to locate and contain the water-swellable material and to separate the magnet 30 from the water-swellable material. The membrane needs to be compliant with much elongation so that it provides very little resistance against the swelling of the water-swellable material 12. The membrane can be made of a flexible rubber euch as latex rubber, silicone rubber, or polyester reinforced buna N rubber, or Teflon.

The device 10 is more sensitive to changes in soil moisture content in the range of from −0.1 to −1 bar when the membrane 28 does not adhere to the water-swellable material than when it does. Further, if the membrane 28 adheres to the water-swellable material on shrinkage, the material sticks to the membrane and then slips apart from the membrane. This stresses the material, resulting in a change in moisture readings even when the moisture content of the soil adjacent the device remains constant. Therefore, preferably the membrane does not strongly adhere to the water-swellable material. This can be effected by selecting a membrane and water-swellable material that do not adhere to each other. Alternatively, as shown in FIG. 3, a barrier sheet 29 can be placed between the membrane 28 and the water-swellable material. A suitable anti-stick barrier sheet 29 is formed from Teflon ™ coated glass fabric, 0.01 inch thick, available from Butler Precision Belting of Santa Clara, Calif., Part Number 7109.

The water-swellable material can be restrained. To restrain the water-swellable material, it can be held in place by an adhesive, impaled in place, combined with a less swellable material, cross-linked into a fixed substrate, clamped in place, or as preferred, rely on the adhesiveness of a polymer to a suitable porous member. For example, a polyacrylamide swellable polymer can adhere directly to an aluminum oxide rigid ceramic porous member.

The water-swellable material can be unrestrained if desired, in the form of powder, beads, spheres, fabric, fibers, sheets, discs, and the like.

Other detection techniques besides use of a magnet and a Hall effect sensor can be used. Generally sensing can be effected with a sensing element such as a Hall effect sensor and an activating element such as a magnet. One of the elements is mounted to move with the water-swellable material as it swells and shrinks and the other element is fixedly mounted. It is preferred that the activating element be mounted to move and that the sensing element be in a fixed position, as shown in FIGS. 1-3, although it is possible to reverse this.

Other sensing techniques that can be used include capacitance, where one capacitor plate is mounted to move with the water-swellable material and the other capacitor plate is fixed. Alternatively, the plates could be fixed with the water-swellable material forming a variable portion of the dielectric inbetween.

Another sensing technique is to load the polymer with a ferro- or ferrimagnetic filler and use small coils to determine the magnetic flux density in the swollen polymer. Alternatively, a ferro- or ferrimagnetic material can be positioned to move with the water-swellable polymer near one or more coils to cause a change in inductance.

Other sensing techniques do not require a separate activator and sensing element. For example, an optical technique can be used where light passes through the water-swellable material. As the water-swellable material expands, more light passes through it. Alternatively, light of a wave length that is absorbed by water can be used. As the water-swellable material absorbs more water, less light passes through. Light in the infrared region having a frequency of 3200 to 3600 cm$^{-1}$ is absorbed by water.

In another optical method, light is reflected off the water-swellable material or a surface moved by the water-swellable material. The distance the light travels can be measured, indicating the amount of swelling that has occurred.

Alternatively, a polymer can be used to move another material or device that causes a resistance change.

The response of the sensing means is not necessarily linearly proportional to the volume change of the water-swellable material. For example, in the version of FIG. 3, initially the water-swellable material swells both laterally and vertically, while the sensor only detects vertical swelling. The sensing means responds linearly to the swelling generally only if the ratio of vertical to lateral swelling of the water-swellable material remains unchanged.

A preferred configuration for using a Hall effect sensor and a magnet is shown in FIGS. 1-3. However, other configurations are possible. For example, rather than using a separate magnet, a water-swellable polymer can be loaded with a magnetic filler. Also, rather than using just a solid magnet, a ferro fluid in combination with a solid magnet can be used.

A preferred magnet for the version shown in FIGS. 1-3 is a rare earth magnet, such as Catalog No.

RE80221 made by Crucible Magnetics Division of Colt Industries of Elizabethtown, Ky.

A suitable Hall effect sensor is available from Sprague Electric Company of Concord, N.H. under Catalog No. UGN-3503. This sensor is a 3-lead linear sensor whose output null voltage is nominally ½ Vcc and whose magnetic to voltage gain is proportional to Vcc. Its sensitivity with an input voltage of 5 V is typically 1.3 MV/gauss. The use of a Hall effect sensor for indicating position is described in U.S. Pat. No. 4,107,604, which is incorporated herein by this reference.

With reference to FIGS. 4 and 5, another soil moisture measuring device 100 includes a cup-shaped upper bulkhead 102 having a base 103 and a lower bulkhead 104 shaped like an inverted cup. The upper bulkhead 102 and lower bulkhead 104 are held together by screws 106. The upper bulkhead includes a circular opening 108 in its bottom adjacent to the lower bulkhead 104. Within this opening 108 is located a porous ceramic disc 110 having a disc of water-swellable polymer 112 mounted thereon. A compliant diaphragm or membrane 114 is located on top of the disc of water-swellable polymer 112.

Mounted on top of the membrane 114 is a capsule 116 having a lower peripheral flange 118 having grooves 119 therethrough for placement of the screws 106 which hold the capsule in place. The peripheral flange 118 holds the edge of the diaphragm 114 clamped to the base 103 of the upper bulkhead 102.

A magnet 120 is mounted on the diaphragm 114 within the capsule 116. A Hall effect sensing device 122 is mounted in the wall of the capsule 116 directly above the magnet 120. Leads 124 extend from the sensor 122 upwardly.

The peripheral wall of both bulkheads 102 and 104 is covered by a wrap-around foam 126 that is water absorbent. Fabric wicks 128 are located between the foam 126 and the bulkheads and extend into the region where the two bulkheads are held together. The fabric wicks are in contact with the porous disc 110 so that moisture can be transmitted through the foam 126 to the fabric wicks 128 and then to the porous ceramic 110 which carries the water to the water-swellable polymer 112.

The device 100 also includes an end cap 130 threaded onto the lower bulkhead 104 and a cylindrical housing member 132 threaded onto the top of the upper bulkhead 102.

This device 100 operates substantially the same as the device 10 shown in FIGS. 1–3. As the water-swellable polymer swells, it causes the magnet 120 to move closer to the Hall effect sensing device 122. The increase in magnetic field resulting from the magnet moving closer to the Hall effect sensing device 122 increases the output from the Hall effect sensing device through the electrical leads 124. This increase in electrical output can be measured by the detector 48, indicating that the moisture content of soil adjacent to the device 100 has increased. The foam 126 and fabric wicks 128 insure that the water-swellable polymer is quickly in equilibrium with the surrounding environment.

There is ample room provided by the device 100 for the water-swellable polymer 112 to swell to its fully swollen state. The chamber 134 defined by the capsule 116, the porous ceramic disc 110, and the base 103 of the upper bulkhead 102 provides ample room for the water-swellable polymer 122 to swell.

With reference to FIGS. 6 and 7, another soil moisture measuring device according to the present invention provides a unique technique for anchoring the water-swellable material to a rigid porous substrate. The device 200 shown in FIGS. 6 and 7 includes a housing formed from a lower housing member member 202 and a mating upper housing member 204 having pins 206 that slide into corresponding openings 208 in the lower housing 202. The two housing members are held together by screws 209. Each housing member has a semi-circular opening 212 in each end wall 210. The semi-circular openings 212 cooperate to form two circular openings which cradle the ends of a rigid, porous, ceramic tube 214. A tube of water-swellable polymer 216 is shrunk onto the exterior surface of the ceramic tube 214. The water-swellable tube 216 is slip fitted onto the ceramic tube 214 while it is at least partly swelled, and preferably fully swelled, so that upon drying and shrinkage, the water-swellable tube firmly remains in place. If desired, the ceramic tube can have a wicking material placed internally such as a tubular water transmitting wad 218.

A flat diaphragm 220 is mounted on top of the water-swellable tube 216. The diaphragm 220 has holes 222 through its peripheral edge and the pins 206 of the upper housing 204 extend through these holes 222 to maintain the diaphragm 220 fixedly in place.

A magnet 224 is secured to the top of the diaphragm 220 and this magnet cooperates with a Hall effect sensing device 226 mounted in the top wall of the upper housing 204 directly above the magnet 224.

As seen in FIG. 7, the upper and lower housing members form a large chamber 228 which provides ample room for complete swelling of the water-swellable tube 216.

FIG. 8 shows circuitry useful for a sensing device based on Hall effect sensors. Two Hall effect sensors 300 are provided, each preferably being a Sprague UGN350A linear Hall effect sensor. The sensors are used back-to-back, bonded together, so that the output of one is subtracted from the other using a differential amplifier 302. This enhances differential-mode magnetic field changes but reduces common-mode heat effects.

These sensors operate off of six volts. Each sensor is provided with a power source comprising two Polaroid lithium power cards 304. These are high-energy-density batteries which can be protected from accidental discharge with a momentary on/off switch 312. Each cell provides six volts initially. A Schottky IN5618 diode 306 is placed in parallel with each cell. These diodes have a low forward voltage drop and low reverse leakage current. These diodes are used because if a lithium cell deteriorates, it often reverses polarity. The Schottky diode protects against fire in case reverse polarity occurs.

The voltage to each sensor 300 is controlled with a voltage regulator 308 to provide about six volts, the voltage required by the sensors 300.

A capacitor 310 is provided across the input of the operational amplifier 302 as a filter to eliminate A-C noise such as that generated by transmission lines. Preferably all electronics are EMI shielded.

The output from the operational amplifier passes to a meter 320 that is provided with a battery check mode (BC). An offset adjustment potentiometer 322 is connected to the minus node of the operational amplifier 302. This offset adjustment potentiometer 322 corrects for the error resulting from the "front" sensor 300 having a −6 volt output relative to the "back" sensor. The potentiometer is also used to compensate for the fully-swollen starting point voltage.

A soil moisture detecting device according to the present invention has significant advantages. It can measure soil moisture matric potential from 0 to −15 bars. It can be designed to be accurate to ±2 centibars in the range of 0 to −1 bar and ±5 centibars in the range of from −1 to −10 bars. Response to change in soil moisture matric potential is fast, and readings are possible at any time and upon demand.

The output is generally free of hysteresis and repeatable. The output from the sensors is analog and electrical so that information from many sensors can be transmitted back to a central control point such as a computer.

The sensor is inexpensive to manufacture, maintain, and operate and is capable of operating in all types of soil, from light sandy soils to heavy clay soils. Calibration is simple and easy, and the sensor measures water available for plant growth.

Although the present invention has been described in considerable detail with reference to certain preferred versions thereof, other versions are possible. For example, the Hall effect sensors can be mounted to the bottom of the device so that as the swellable material swells, the output from the sensors decreases. Also, the magnet 30 can be left out of the apparatus by using a magnetic membrane 28. Therefore the spirit and scope of the appended claims should not necessarily be limited to the description of the preferred versions contained herein.

What is claimed is:

1. An apparatus for measuring humidity comprising:

(a) a rigid, porous, cylindrical substrate, the substrate being capable of passing water therethrough;
   (b) a tube of water-swellable polymer in contact with the cylindrical substrate, the water-swellable polymer having a fully swollen volume when in its fully swollen state in equilibrium with water at least about 2 times its dry volume, said tube and substrate being substantially completely contained in a chamber, the volume of the chamber being sufficiently large to accomodate the tube in its fully swollen state; and
   (c) sensing means responsive to the volume of the water-swellable polymer for producing a signal that varies with the water content of the environment exterior to the chamber.

2. The apparatus of claim 1 in which the substrate is a porous ceramic material.

3. The apparatus of claim 1 in which the substrate is tubular.

4. The apparatus of claim 3 including a water wicking material in the interior of the tubular substrate.

5. The apparatus of claim 1 wherein (a), (b) and (c) are arranged such that the external resistance, if any, to swelling of the water-swellable polymer remains substantially constant as the water-swellable polymer swells to its fully swollen state.

6. The apparatus of claim 1 including sensing means responsive to the volume of the water-swellable polymer for producing a signal proportional to the water content of the environment around the water-swellable polymer.

7. The apparatus of claim 1 which the water-swellable polymer is shrunk into contact with the cylindrical substrate.

* * * * *